US00PP27003P3

(12) United States Plant Patent
Schoone

(10) Patent No.: US PP27,003 P3
(45) Date of Patent: Aug. 2, 2016

(54) ***PHALAENOPSIS* ORCHID PLANT NAMED 'FLOR182631'**

(50) Latin Name: *Phalaenopsis hybrida*
Varietal Denomination: FLOR182631

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 138 days.

(21) Appl. No.: 13/999,403

(22) Filed: Feb. 24, 2014

(65) Prior Publication Data

US 2014/0317806 P1 Oct. 23, 2014

Related U.S. Application Data

(60) Provisional application No. 61/814,970, filed on Apr. 23, 2013.

(30) Foreign Application Priority Data

Apr. 25, 2013 (NL) ..... OPS1026

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

The RHS International Orchid Registry *Phalaenopsis* 'Pink Glow' retrieved on Aug. 27, 2015, retrieved from the Internet at <http://apps.rhs.org.uk/horticulturaldatabase/orchidregister/orchiddetails.asp?ID=30861> pp. 3-5.*
Hew et al The Physiology of Tropical Orchids in Relation to the Industry 2nd ed. 2004, p. 33.*
First Rays LLC Register your Hybrid, retrieved on Jan. 5, 2016, retrieved from the Internet at <http://firstrays.com/free-information/miscellaneous-stuff/register-your-hybrid/> 2 pp.*
Wikia *Phalaenopsis sanderiana*, retrieved on Jan. 4, 2016, retrieved from the Internet at <http://storczyki.wikia.com/wiki/Phalaenopsis_sanderiana> 4 pp.*
Wikia *Phalasenopsis sanderiana* English translation, 2 pp.*

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'FLOR182631' particularly characterized by flowers which are white with a purple/violet mark in the center; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'FLOR182631'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'FLOR182631'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'FLOR182631' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'FLOR182631' originated from a cross made by the inventor in 2000 in Strengweg, Heemskerk, The Netherlands. The female or seed parent is the *Phalaenopsis* cultivar designated 'Maki Watanabe', unpatented. The male or pollen parent is the *Phalaenopsis* cultivar designated (Taisuco Windian×Otohime), unpatented. The new *Phalaenopsis* 'FLOR182631' was discovered and selected by the inventor as a single flowering plant within the progeny of the stated cross in a controlled environment in 2008 in Strengweg, Heemskerk, The Netherlands.

Asexual reproduction of the new *Phalaenopsis* cultivar by tissue culture (mericloning) was first performed in November, 2008 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'FLOR182631', which in combination distinguish this *Phalaenopsis* as a new and distinct cultivar:

1. flowers which are white with a purple/violet mark in the center;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'FLOR182631', the female parent 'Maki Watanabe' has white colored flowers with a purple center, the male parent (Taisuco Windian×Otohime) has white colored flowers, whereas the flowers of 'FLOR182631' are white with a purple/violet haze in the center.

Presently, the commercial cultivar to which 'FLOR182631' can be meaningfully compared is 'Lark Song' (unpatented). The flowers of 'FLOR182631' are white with a purple/violet haze, whereas the flowers of 'Lark Song' are light purple with some white at the edges.

BRIEF DESCRIPTION OF THE PHOTOGRAPHS

The accompanying photographs illustrate the overall appearance of the new *Phalaenopsis* 'FLOR182631' showing the colors as true as is reasonably possible with colored reproductions of this type. Colors in the photographs may differ slightly from the color values cited in the detailed botanical description, which accurately describe the color of 'FLOR182631'.

DETAILED BOTANICAL DESCRIPTION

Figure 1:
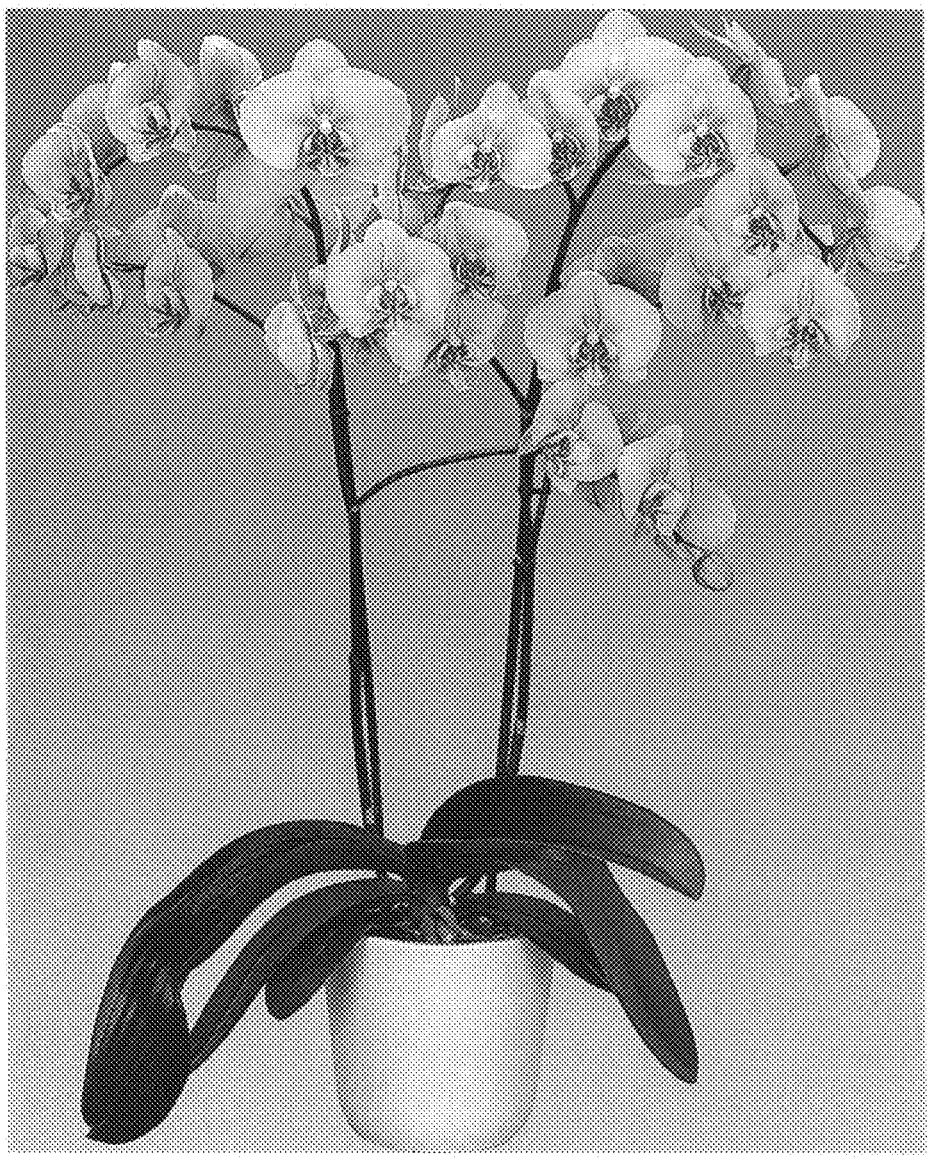
FIG. 1 shows a side view perspective of a typical flowering plant of 'FLOR182631' in a 12 cm pot, at 16 months of age.

The new *Phalaenopsis* cultivar 'FLOR182631' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'FLOR182631' as grown in a greenhouse in Strengweg, Heemskerk, The Netherlands, under conditions which closely approximate those generally used in commercial practice. Initially, the ideal temperature to grow plants of 'FLOR182631' is 27° C. during the day and at night. Then, during the flowering phase of 'FLOR182631', the ideal growing temperature is 20-22° C. during the day and 18° C. at night. Light levels for growing 'FLOR182631' are a minimum of 5,000 lux and a maximum of 10,000 lux. A balanced fertilizer with level of 200 ppm N, 87 ppm P, 168 ppm K is applied. Duration of growth of 'FLOR182631' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'FLOR182631' plants described is 12 months after potting.

Classification:

*Botanical.—Phalaenopsis hybrida.*

Parentage:

*Female or seed parent.—Phalaenopsis* cultivar designated 'Maki Watanabe', unpatented.

*Male or pollen parent.—Phalaenopsis* cultivar designated (Taisuco Windian×Otohime), unpatented.

Propagation:

*Type*.—Tissue culture (mericloning).

*Rooting habit and description*.—Fleshy; approximately 4 mm-6 mm wide and greyed/green (RHS 188B and RHS 189A) and a little green (RHS N137A) in color; freely branching. It takes 12 weeks for plants growing in tissue culture to initiate roots.

Plant:

*Size at maturity*.—Height (from bottom of pot to highest flower): about 65 to 75 cm. Spread: about 65 cm.

*Growth habit*.—Standard; green leaves (RHS 137A) and a relatively normal raceme.

*Vigor*.—Moderate.

*Crop time*.—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant*.—About 5 to 8 leaves are produced before flowering.

*Arrangement and attachment*.—Alternate, clasping.

*Overall shape of leaf*.—Oval, the tip is blunt and asymmetric.

*Texture* (*upper & underside*).—Smooth and leathery.

*Pubescence*.—None.

*Mature leaf length*.—About 20 to 27 cm.

*Mature leaf width*.—About 6 to 10 cm.

*Mature leaf thickness*.—About 2 mm.

*Mature leaf color*.—Upper side: green (RHS 137A). Under side: yellow/green (RHS 146A).

*Leaf base*.—Acute.

*Margin*.—Entire.

*Venation*.—Pattern: parallel. Color of midvein: upper side: green (RHS 137A). under side: yellow/green (RHS 146A).

Inflorescence description:

*Appearance*.—Upright to slightly pendant, racemose inflorescence with bilaterally symmetrical flowers that open in succession beginning with the lowermost flower.

Raceme:

*Quantity per plant*.—About 1 to 2.

*Number of flowers per raceme*.—About 15 to 25.

*Length*.—About 65 cm.

*Peduncle*.—Diameter: about 6 mm. Strength: strong. Aspect: upright. Texture: glabrous and smooth. Color: brown (RHS N200A) with yellow/green (RHS 146A and RHS 147A).

*Buds*.—Height (from base to tip): about 20 mm. Diameter (at midpoint): about 17 mm. Shape: oval. Color: yellow/green (RHS 145B) with a purple/violet haze (RHS N80C).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Flower:

*Rate of opening*.—Flowers fully opened about 2 to 3 days after petal and sepal separation.

*Orientation at opening*.—Slanted upward and outward.

Figure 2:
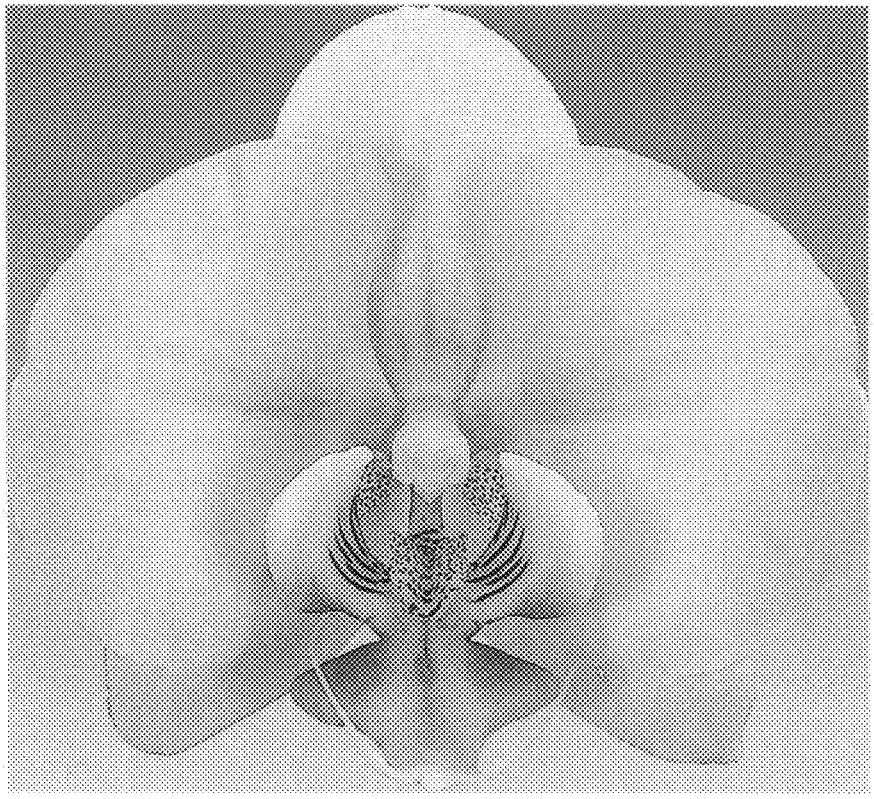
FIG. 2 shows a close-up view of a typical flower of 'FLOR182631'.
Figure 3:
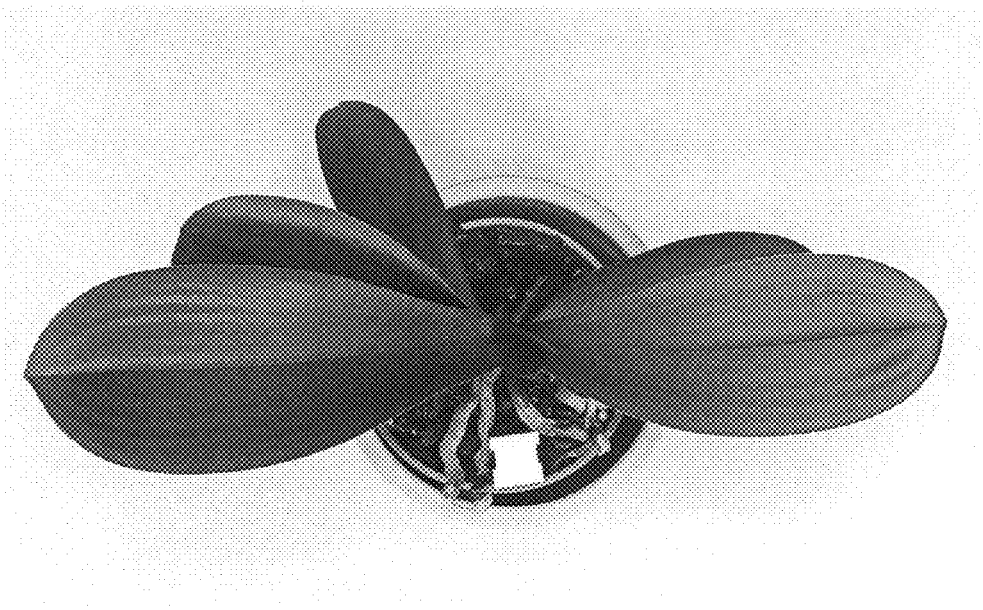
FIG. 3 shows a close-up view of the typical leaves of 'FLOR182631'.

*Shape*.—Typical shape of *Phalaenopsis*; see FIG. 2.

*Size* (*of single bloom*).—Height: about 65 to 95 mm. Diameter: about 60 to 100 mm.

*Quantity and arrangement*.—Three petals and three sepals that are trimerous, and arranged in 2 overlapping whorls. Inner whorl of 3 petals is comprised of 2 lateral petals and a labellum. Petals are more pronounced than sepals.

Petals:

2 *lateral petals*.—Overall shape: broadly ovate and weakly cupped. Apex: oval with a little notch. Margin: entire and weakly undulate. Base: broadly ovate. Length: about 55 mm. Width: about 45 mm. Texture: Upper surface: smooth and satiny. Under surface: smooth and satiny. Color (when fully opened): upper surface: white (RHS NN155C) with a the base a purple/violet mark (RHS N80B and RHS N80C). Under surface: white (RHS NN155C). At the base a light purple/violet haze (RHS N80B and RHS N80C). Some also have a light green/yellow haze (RHS 145D) over the whole petal.

*Labellum*.—Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: oval. Length midlobe: about 20 mm. Width midlobe (not flattened): about 25 mm. Length lateral lobe: about 17 mm. Width lateral lobe(not flattened): about 15 mm. Texture: Upper and under surface: smooth and satiny. Color (when fully opened): Mid lobe, upper surface: white (RHS NN155C); the mid vein is yellow (RHS 6D) and from the base a small red/purple stripe (RHS 61A). The corners are yellow/orange (RHS 14C) with red/purple (RHS 61A). Some corners are a little lighter yellow (RHS 7D). Under surface: white (RHS NN155D). The mid vein is yellow (RHS 6D) and the corners are yellow (RHS 14B) with a red/purple edge (RHS 61A). Lateral lobes, upper surface: white (RHS NN155C); from the base red/purple stripes (RHS 59A). Part of the lower edge is yellow (RHS 12A) with a the beginning a small red/purple edge and some spots (RHS 61A). Under surface: white (RHS NN155C). The lower edge is yellow (RHS 12A) with a little red/purple (RHS 61A). At the upper edge is a little greyed/orange mark (RHS 172D).

*Cirrhi*.—About 23 mm and curly. Color: white (RHS NN155C), then yellow (RHS 6D) which runs into yellow (RHS 12A).

*Pestle* (*callosities*).—Length: about 5 mm. Width (not flattened): about 7 mm. Pubescence: None. Color: main color is white (RHS NN155C) with red/purple stripes and spots (RHS 59A). Front and top are yellow (RHS 12A).

Sepals:

*Arrangement*.—Outer whorl comprises 3 sepals, one dorsal and two lateral sepals.

*Overall shape*.—Elliptical and weakly cupped. Margin: entire and weakly undulate. Length: about 45 mm. Width: about 35 mm. Apex: oval; lateral sepals little pointy. Texture: Upper and under surface: smooth and satiny. Color (when fully opened): Dorsal, upper surface: white (RHS NN155C) with some purple/violet (RHS N80B and RHS N80C). Under surface: white (RHS NN155C) with a purple/violet haze (RHS N80D) and some yellow/green (RHS 145C and RHS 145B). Lateral, upper surface: white (RHS NN155C) with some red/purple spots (RHS 71A) and a green/white haze (RHS 157A). At the base a purple/violet haze (RHS N80D). Under surface: yellow/green (RHS 145B and RHS 145C). Edges are white (RHS NN155C) with a purple/violet haze (RHS N80B and RHS N80C).

Pedicel:

*Length*.—About 20 to 41 mm.

*Diameter*.—About 3 mm.

*Texture*.—Glabrous and smooth.

*Color*.—Green/white (RHS 157B) with a red/purple haze (RHS 70A). Closer to the raceme yellow/green (RHS 145A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed or fruit.

*Column*.—Length: about 10 mm. Diameter: about 7 mm. Color: white (RHS NN155C). At the base a purple/violet haze (RHS N80D).

*Pollinia*.—Quantity: two. Diameter: about 2 mm. Color: yellow/orange (RHS 22A).

*Ovary*.—Length: about 4 mm. Diameter: about 6 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

The invention claimed is:

1. A new and distinct *Phalaenopsis* plant named 'FLOR182631', as illustrated and described herein.

* * * * *